US007057073B2

(12) United States Patent
Mitchell et al.

(10) Patent No.: US 7,057,073 B2
(45) Date of Patent: Jun. 6, 2006

(54) SYNTHESIS OF TRINITROPHLOROGLUCINOL AND TRIAMINOTRINITROBENZENE (TATB)

(75) Inventors: Alexander R. Mitchell, Livermore, CA (US); Michael D. Coburn, Santa Fe, NM (US); Gregory S. Lee, San Ramon, CA (US); Robert D. Schmidt, Livermore, CA (US); Philip F. Pagoria, Livermore, CA (US); Peter C. Hsu, Pleasanton, CA (US)

(73) Assignee: Regents of the University of California, Oakland, CA (US)

( * ) Notice: Subject to any disclaimer, the term of this patent is extended or adjusted under 35 U.S.C. 154(b) by 39 days.

(21) Appl. No.: 10/912,723

(22) Filed: Aug. 4, 2004

(65) Prior Publication Data

US 2005/0070743 A1    Mar. 31, 2005

Related U.S. Application Data

(60) Provisional application No. 60/492,705, filed on Aug. 4, 2003.

(51) Int. Cl.
C07C 209/18    (2006.01)
C07C 211/50    (2006.01)
C07C 205/06    (2006.01)
(52) U.S. Cl. .................. 564/403; 564/441; 568/710
(58) Field of Classification Search ................. 568/710
See application file for complete search history.

(56) References Cited

U.S. PATENT DOCUMENTS

| 4,032,377 | A | | 6/1977 | Benziger |
| 4,434,304 | A | * | 2/1984 | DeFusco et al. ............ 568/710 |
| 4,794,197 | A | * | 12/1988 | Schneider et al. .......... 564/152 |
| 5,569,783 | A | | 10/1996 | Mitchell et al. |
| 5,633,406 | A | | 5/1997 | Mitchell et al. |
| 6,069,277 | A | | 5/2000 | Mitchell et al. |

FOREIGN PATENT DOCUMENTS

| GB | 2 355 713 | 10/1999 |
| GB | 2 355 715 | 10/2000 |

OTHER PUBLICATIONS

Database CAPLUS on STN, Acc. No. 2001:263672, Mitchell et al., NATO Science Series, II: Mathematics, Physics and Chemistry (2000), 3 (Applications of Demilitarized Gun and Rocket Propellants in Commercial Explosives), p. 49-57 (abs).*

Database CAPLUS on STN, Acc. No. 1998:435057, Mitchell et al., Challenges in Propellants and Combustion: 100 Years after Nobel, [International Symposium on Special Topics in Chemical Propulsion], 4th, Stockholm, May 27-31, 1996 (1997), p. 189-198 (abs).*

(Continued)

*Primary Examiner*—Brian J. Davis
(74) *Attorney, Agent, or Firm*—Ann Lee; Alan H. Thompson

(57) ABSTRACT

A method to convert surplus nitroarene explosives into trinitrophloroglucinol and triaminotrinitrobenzene (TATB) is described. Picric acid is directly aminated to diaminopicric acid, which is converted to trinitrophloroglucinol and triaminotrinitrobenzene.

2 Claims, 3 Drawing Sheets

OTHER PUBLICATIONS

Database CAPLUS on STN, Acc. No. 1996:514515, Mitchell et al., International Annual Conference of ICT (1996), 27th (Energetic Materials), 29.1-29.11 (abs).*

J.Jens Wolff and H.H. Limbach Synthesis and Spectroscopic Characterization of $^{15}$N-Labeled Hexaaminobenzene Derivatives; Liebigs Ann. Chem.(1991) 691-693.

Philip F. Pagoria et al 1,1,1-Trimethylhydrazinium Iodide: A Novel, Highly Reactive Reagent for Aromatic Amination via Vicarious Nucleophilic Substitution of Hydrogen; J. Org. Chem. (1996)2934-2935.

Anthony J. Bellamy et al A New Synthetic Route to 1,3,5-Triamino-2,4,6-Trinitrobenzene (TATB); Propellants, Explosives, Pyrotechnics; 27, pp. 49-58, (2002).

* cited by examiner

US 7,057,073 B2

SYNTHESIS OF TRINITROPHLOROGLUCINOL AND TRIAMINOTRINITROBENZENE (TATB)

CLAIM OF PRIORITY IN PROVISIONAL APPLICATION

This application is related to Provisional Application No. 60/492,705 filed Aug. 4, 2003 entitled "Method to Synthesize Trinitrophloroglucinol and TATB", and claims priority thereto under 35 USC 120. Provisional Application No. 60/492,705 is herein incorporated by reference in its entirety.

The United States Government has rights in this invention pursuant to Contract No. W-7405-ENG-48 between the United States Department of Energy and the University of California for the operation of Lawrence Livermore National Laboratory.

BACKGROUND

The global demilitarization of munitions is producing millions of pounds of surplus explosives. Historically, surplus explosives have been disposed of by open burning/open detonation (OB/OD). The disposal of these materials by OB/OD is becoming unacceptable due to public concerns and increasingly stringent environmental regulations.

Triaminotrinitrobenzene (TATB) is a reasonably powerful high explosive that's thermal and shock stability is considerably greater than that of any other known material of comparable energy (S. F. Rice et al., "The Unusual Stability of TATB: A Review of the Scientific Literature", Lawrence Livermore National Laboratory, Livermore, Calif., UCRL-LR-103683, July 1990). It is used in military applications because of its significant insensitivity to thermal and shock environments (B. M. Dobratz, "The Insensitive High Explosive Triaminotrinitrobenzene (TATB): Development and Characterization—1888 to 1994," Los Alamos Scientific Laboratory, Los Alamos, N.Mex., Report LA-13014-H, August, 1995). In the civilian sector, perforating guns containing TATB have been designed for deep oil well explorations where heat-insensitive explosives are required. (W. E. Voreck, et al, "Shaped Charge for a Perforating Gun Having a Main Body of Explosive Including TATB and a Sensitive Primer", U.S. Pat. No. 5,597,974). TATB is also used to produce benzenehexamine, an intermediate in the synthesis of new, advanced materials. (See D. Z. Rogers, "Improved Synthesis of 1,4,5,8,9,12-Hexaazatriphenylene," J. Org. Chem., 51, 3904 (1986) and R. Breslow, et al, "Synthesis of the Hexaminobenzene Derivative Hexaazaoctadecahydrocoronene (HOC) and Related Cations, J. Am. Chem. Soc., 106, 6453 (1984). In addition, the use of TATB to prepare components of liquid crystals for use in display devices has been described (K. Praefcke and B. Kohne, "Amido Compounds as Components of Lyotropic Liquid-Crystal Phases, Ger. Offen. DE 3,612,238 (1988); Chemical Abstracts, 108, 159109n.)

SUMMARY OF THE INVENTION

Disclosed herein is a method to synthesize trinitrophloroglucinol and triaminotrinitrobenzene (TATB) from inexpensive, surplus nitroarene explosives such as picric acid and ammonium picrate (Explosive D). Direct amination of picric acid by vicarious nucleophilic substitution (VNS) of hydrogen yields diaminopicric acid. Treatment of diaminopicric acid with sodium hydroxide in water or water-DMSO mixtures produces, upon neutralization with acid, trinitrophloroglucinol. The direct conversion of diaminopicric acid to TATB is also disclosed.

BRIEF DESCRIPTION OF THE DRAWINGS

The accompanying drawing, which is incorporated into and form part of this disclosure, illustrate embodiments of the invention and together with the description, serves to explain the principles of the invention.

DETAILED DESCRIPTION OF THE INVENTION

Figure 1:
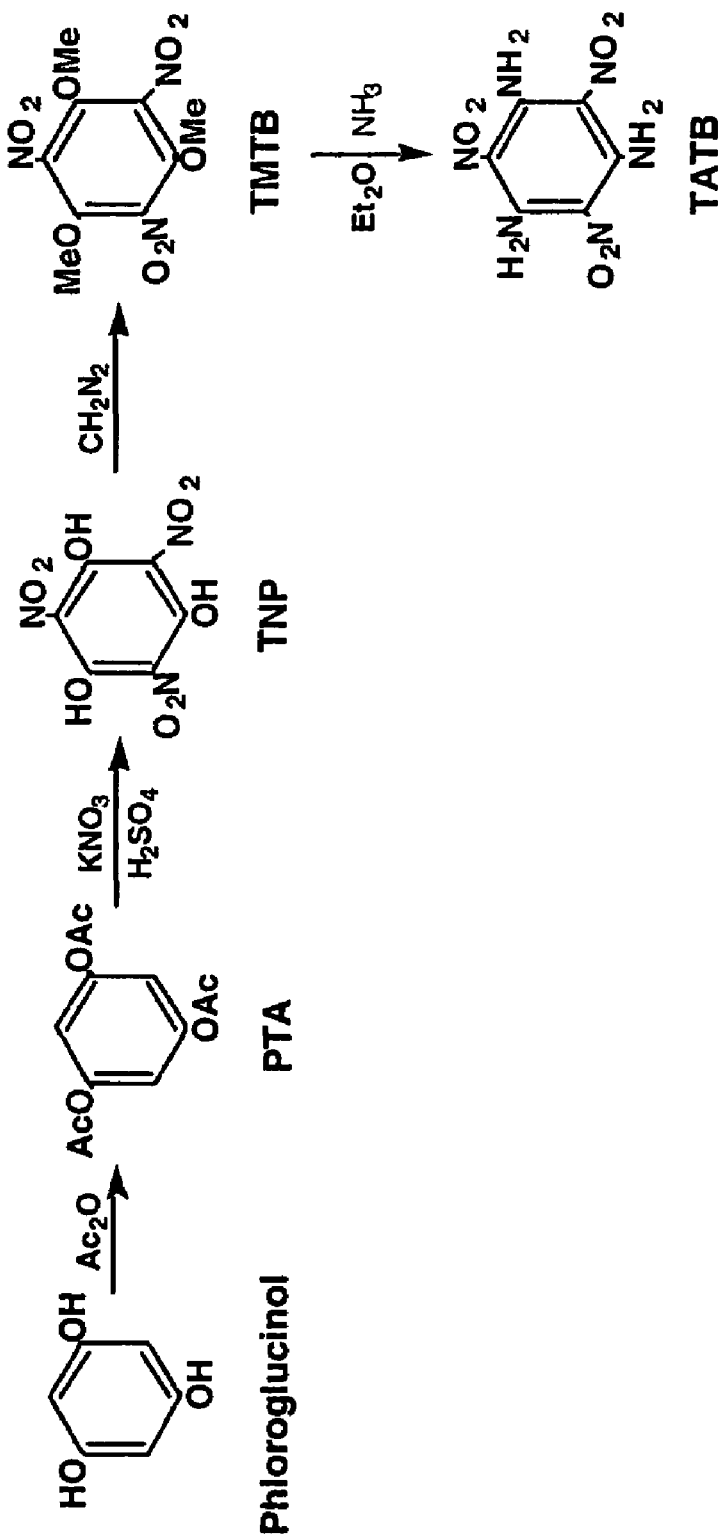
FIG. 1 shows the prior art synthesis of trinitrophloroglucinol (TNP) and trianimotrinitrobenzene (TATB).

Disclosed herein are the conversions of picric acid into diaminopicric acid and trinitrophloroglucinol and their subsequent conversion into TATB. The preparation of trinitrophloroglucinol and its conversion to TATB was first described by Wolff and Limbach ("Synthesis and Spectroscopic Characterization of $^{15}$N-Labeled Hexaminobenzene Derivatives," Liebigs Ann. Chem., 1991, p. 691). Referring to FIG. 1, phloroglucinol is converted to phloroglucinol triacetate (PTA), which is then nitrated to trinitrophloroglucinol (TNP, 93%) using a stoichiometric quantity of potassium nitrate in sulfuric acid at room temperature. Excess diazomethane converts TNP to 1,3,5-trimethoxy-2,4,6-trinitrobenzene (TMTB, 100%), which is then ammonolyzed using a 1.6-fold excess of ammonia in ether with warming from −78° to 70° C. to give TATB (97%).

Bellamy and coworkers later modified the Wolff-Limbach preparation of TATB by replacing the alkylating reagent (diazomethane) used to convert TNP to TMTB with either dimethyl sulfate or a trialkyl orthoformate (A. J. Bellamy, et al, "Synthesis of Diamino- or Triamino-2,4,6-trinitrobenzene," UK Patent Applications GB 2,355,713 A and GB 2,355,715 A and A. J. Bellamy, et al, "A New Synthetic Route to 1,3,5-Triamino-2,4,6-Trinitrobenzene (TATB)," Propellants, Explosives, Pyrotechnics, vol. 27, 49, 2002).

The major shortcoming to the Wolff-Limbach and Bellamy syntheses of trinitrophloroglucinol and TATB modification is economic. The starting material (phloroglucinol) is about $50/lb (bulk quantities). It is unlikely that the 4-step process will be competitive with processes utilizing significantly less expensive starting materials.

The method disclosed herein starts with picric acid, which is available from the demilitarization inventory or the world market at about $1/lb, roughly 1/50 of the cost of phloroglucinol. Picric acid is aminated to diaminopicric acid (DAP) using VNS chemistry described earlier [A. R. Mitchell, et al, U.S. Pat. Nos. 5,569,783 and 5,633,406 and 6,069,277 and P. F. Pagoria, et al, "1,1,1-Trimethylhydrazinium Iodide (TMHI): A Novel, Highly Reactive Reagent for Aromatic Amination via Vicarious Nucleophilic Substitution of Hydrogen," J. Org. Chem., 61, 2934, 1996].

Figure 2:
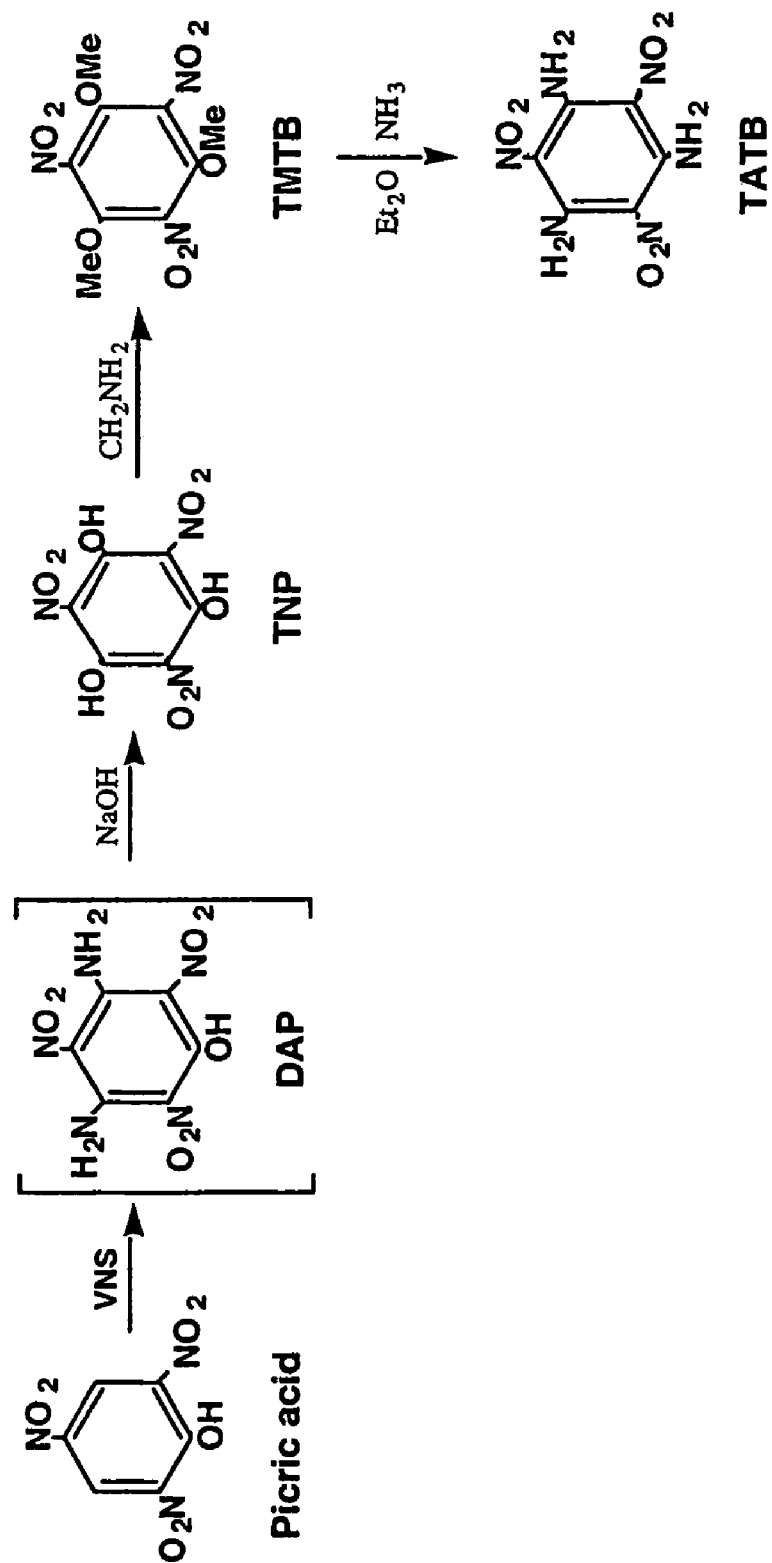
FIG. 2 shows the conversion of picric acid to diaminopicric acid (DAP) to TATB via trinitrophloroglucinol (TNP).
Figure 3:
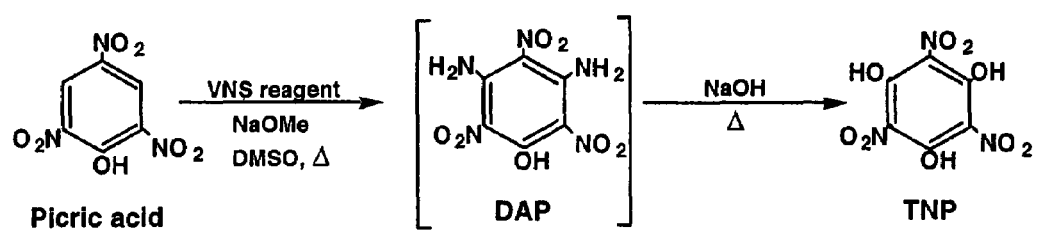
FIG. 3 shows the conversion of picric acid to trinitrophloroglucinol (TNP) via diaminopicric acid (DAP).
Figure 4:
FIG. 4 shows the direct conversion of diaminopicric acid (DAP) to TATB.

Referring to FIG. 2, picric acid, 4-amino-1,2,4-triazole (ATA) and sodium methoxide react in a mixture of methanol, toluene and DMSO to produce diaminopicric acid (DAP) in 68% yield (Example 1). Replacement of ATA with 1,1,1-trimethylhydrazinium chloride, a more active VNS reagent, affords DAP in 91% yield. DAP is heated in aqueous base (e.g., an alkyl hydroxide) and acidified to yield trinitrophloroglucinol (TNP) in 84% yield (Example 2). Picric acid is converted to TNP (67%) without isolation of DAP when aqueous base is added to the reaction mixture at the conclusion of the VNS reaction of picric acid with ATA (Example 3). Referring to FIG. 3, TNP can be produced from picric acid via DAP. TNP, when produced from inexpensive picric acid rather than the more costly phloroglucinol, can be utilized in the Wolff-Limbach or Bellamy syntheses to produce TATB at significant cost savings as well as other industrial important materials. Referring to FIG. 4, greater cost savings can be realized when diaminopicric acid (DAP) is directly converted to TATB. The reaction of DAP with diammonium hydrogen phosphate to directly afford TATB is disclosed in Example 4.

The following Examples are to explain and describe the invention. They are not to be construed to be limiting in any way.

EXAMPLE 1

(a) Picric acid (0.275 g, 1.20 mmol) and 4-amino-1,2,4-triazole (0.504 g, 6.00 mmol) are dissolved in a mixture of DMSO (3.6 ml) and toluene (4.8 ml) and a 25 wt. % solution of sodium methoxide in methanol (3.00 ml, 13.1 mmol) is added. The resulting suspension produced a lemon-yellow suspension is stirred and heated from ambient temperature to 95° C. over a one hour period. The suspension is cooled to 4° C., treated with glacial acetic acid (14 ml) and warmed to ambient temperature with stirring. The resulting precipitate is collected and washed with acetic acid and water. Vacuum drying (80° C.) gives 0.176 g of diaminopicric acid. An additional 0.034 g of product is isolated from the acetic acid-water washes to give a total of 0.210 g of diaminopicric acid (68% yield). The IR spectra for this material and known diaminopicric acid (W. M. Koppes, et al, "Reaction of 1,3,5-trifluorotrinitrobenzene with nucleophiles," Journal of the Chemical Society-Perkin Transactions 1, 1815, 1981) are identical.

(b) The use of 1,1,1-trimethylhydrazinium halide, a more active VNS reagent, in place of 4-amino-1,2,4-triazole affords a conversion of picric acid to diaminopicric acid in 91% yield.

EXAMPLE 2

Diaminopicric acid (0.100 g, 0.386 mmol) is suspended in water (6.85 ml) and a 50% aqueous solution of sodium hydroxide (0.65 ml,12.5 mmol) is added. The suspension is stirred for 0.5 hr in a heated water bath (98–100° C.) to produce an orange-red suspension which is cooled to 4° C. Addition of cold 12N hydrochloric acid (4 ml) produces a deep yellow suspension that is heated to solution. Cooling to 4° C. produces orange-yellow crystals (needles) that are collected, washed with cold 3N hydrochloric acid and dried to give trinitrophloroglucinol (0.085 g) in 84% yield. The IR spectrum for this material corresponds to that for known trinitrophloroglucinol.

EXAMPLE 3

Picric acid (0.27 g, 1.20 mmol) and 4-amino-1,2,4-triazole (0.504 g, 6.00 mmol) are dissolved in a mixture of DMSO (3.6 ml) and toluene (4.8 ml) and treated with a 25 wt. % solution of sodium methoxide in methanol (3.00 ml, 13.1 mmol). The resulting suspension is stirred and heated from ambient temperature to 95° C. over a one hour period. The reaction suspension is cooled to ambient temperature prior to the addition of water (22.5 mL) and a 50% aqueous solution of sodium hydroxide (1.95 ml, 37.2 mmol). The brick-red suspension is stirred for 0.5 hour in a heated water bath (98–100° C.) and cooled in an ice bath for several hours. The resulting suspension is filtered and the resulting orange solid (trinitrophloroglucinol sodium salt) is collected and dissolved in hot 3N hydrochloric acid (16 ml). The resulting solution is cooled to ambient temperature prior to storage at 4° C. The crystalline product is collected, washed with cold 3N hydrochloric acid and dried to give trinitrophloroglucinol (0.211 g) in 67% overall yield.

EXAMPLE 4

Diaminopicric acid (0.193 g, 0.748 mmol) and diammonium hydrogen phosphate (0.990 g, 7.50 mmol) are suspended in dry sulfolane (3 ml) and stirred in a Teflon® capped glass pressure tube (8 ml). The suspension is heated with stirring from ambient temperature to 177° C. over a 2 hr period. Stirring and heating (177° C.) is continued for an additional 6 hours. The reaction tube is cooled to 4° C. and the resulting suspension is mixed with water (40 ml). The precipitated product is collected, washed with water and dried to yield TATB in the form of a brown solid (0.154 g, 80%).

Throughout this application, various publications, patents, and published patent applications were referred to. The disclosures of the publications, patents, and published patent specifications referenced in this application are hereby incorporated by reference into the present disclosure to more fully describe the state of the art to which this invention pertains.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

While various materials, parameters, operational sequences, etc. have been described to exemplify and teach the principles of this invention, such are not intended to be limited. Modifications and changes may become apparent to those skilled in the art; and it is intended that the invention be limited only by the scope of the appended claims.

The invention claimed is:

1. A method comprising:
    reacting at elevated temperature a suspension of diaminopicric acid in water and an aqueous alkyl hydroxide to form a reaction product; and
    acidifying said reaction product to produce trinitrophloroglucinol.

2. A method comprising:
    suspending diaminopicric acid and diammonium hydrogen phosphate in dry sulfolane;
    heating the suspension with stirring;
    cooling the suspension; and
    mixing the cooled suspension with water to produce TATB.

* * * * *